United States Patent
Wang et al.

(10) Patent No.: US 7,972,851 B2
(45) Date of Patent: *Jul. 5, 2011

(54) LIVER SPECIFIC CHIMERIC REGULATORY SEQUENCE AND USE THEREOF

(75) Inventors: Mei-Chih Wang, Toufen Township, Miaoli County (TW); Chin-Yu Lin, Jhongpu Township, Chiayi County (TW); Hui-Ti Lin, Sindian (TW)

(73) Assignee: Industrial Technology Research Institute, Hsinchu (TW)

( * ) Notice: Subject to any disclaimer, the term of this patent is extended or adjusted under 35 U.S.C. 154(b) by 479 days.

This patent is subject to a terminal disclaimer.

(21) Appl. No.: 11/600,796

(22) Filed: Nov. 17, 2006

(65) Prior Publication Data

US 2007/0072172 A1    Mar. 29, 2007

Related U.S. Application Data

(63) Continuation-in-part of application No. 11/030,110, filed on Jan. 7, 2005, now Pat. No. 7,157,571.

(30) Foreign Application Priority Data

Sep. 30, 2004  (TW) .............................. 93129594 A

(51) Int. Cl.
  *C12N 5/00*   (2006.01)
  *C12N 5/0735* (2006.01)
  *C12N 5/10*   (2006.01)
  *C12N 5/22*   (2006.01)
  *C12N 15/00*  (2006.01)
  *C07H 21/04*  (2006.01)

(52) U.S. Cl. ........ 435/378; 435/455; 435/370; 435/366; 536/24.1

(58) Field of Classification Search .......................... None
See application file for complete search history.

(56) References Cited

U.S. PATENT DOCUMENTS

| 5,804,407 A | 9/1998 | Tamaoki et al. | |
| 6,254,862 B1 | 7/2001 | Little et al. | |
| 2002/0127715 A1* | 9/2002 | Benvenisty et al. | 435/366 |
| 2002/0160511 A1* | 10/2002 | Rambhatla et al. | 435/370 |
| 2003/0017139 A1 | 1/2003 | Souza et al. | |

FOREIGN PATENT DOCUMENTS

CA      2134994      5/1995

OTHER PUBLICATIONS

Yin et al. AFP(+), ESC-derived cells engraft and differentiate into hepatocytes in vivo. Stem Cells, vol. 20, pp. 338-346, 2002.*
Alam and Cook. "Reporter genes for monitoring gene expression in mammalian cells." Gene Transfer and Expression in Mammalian Cells. Ed. S.C. Makrides. Elsevier Science B.V., 2003. 291-308.*
Yoshitake Hayashi, Jeannie Chan, Hidekazu Nakabayashi, Tomoko Hasimoto, and Taiki Tamaoki, "Identification and Characterization of Two Enhancers of the Human Albumin Gene", The Journal of Biological Chemistry, vol. 267, No. 21, issue of Jul. 25, 1992, pp. 14580-14585.
Kazutada Watanabe, Akira Saito and Taiki Tamaoki, "Cell-specific Enhancer Activity in a Far Upstream Region of the Human α-Fetoprotein Gene", The Journal of Biological Chemistry, vol. 262, No. 10, issue of Apr. 5, 1987, pp. 4812-4818.
Su et al. Selective killing of AFP-positive hepatocellular carcinoma cells by adeno-assocaited virus transfer of the herpes simplex virus thymidine kinase gene. Hum Gene Ther. vol. 7, No. 4, pp. 463-470, Mar. 1996.
Elyse R. Groupp, et al. Characterization of the Distal Alpha Fetoprotein Enhancer, a Strong, Long Distance, Liver-Specific Activator; The Journal of Biological Chemistry, Sep. 2, 1994; pp. 22178-22187; vol. 269, No. 35, U.S.A.

* cited by examiner

*Primary Examiner* — Jennifer Dunston
(74) *Attorney, Agent, or Firm* — Bacon & Thomas, PLLC

(57) ABSTRACT

The present invention relates to a chimeric regulatory sequence with liver cell specificity. The chimeric regulatory sequence includes a proximal regulatory sequence and a distal enhancer 5' flanking region of human α-fetoprotein (AFP) gene. The chimeric regulatory sequence is useful in purified specific lineages, such as liver cells, from other cell lineages.

20 Claims, 8 Drawing Sheets

LIVER SPECIFIC CHIMERIC REGULATORY SEQUENCE AND USE THEREOF

This application is a continuation-in-part application of U.S. application Ser. No. 11/030,110, now U.S. Pat. No. 7,157,571, filed Jan. 7, 2005 (of which the entire disclosure of the prior application is hereby incorporated by reference).

BACKGROUND OF THE INVENTION

1. Field of the Invention

The invention relates to a regulatory sequence which mediate a specific expression in liver cells. Moreover, the invention relates to the use of the regulatory sequences.

2. Description of Related Art

α-fetoprotein (AFP) is a plasma fetal protein, the expression of which is primarily restricted to developing tissues of endodermal origin (yolk sac, fetal liver, and gut), although the level of its expression varies greatly depending on the tissue and the developmental stage. AFP is of clinical interest because the serum concentration of AFP is elevated in a majority of hepatoma patients, with high levels of AFP found in patients with advanced disease. The serum AFP levels in patients appear to be regulated by AFP expression in hepatocellular carcinoma but not in surrounding normal liver. Thus, the AFP gene appears to be regulated to hepatoma cell-specific expression.

Previous studies have revealed a complex regulatory mechanisms to promote the temporal and tissue-specific expression of the AFP gene (Wen et al. *Nucleic Acids Res.* 21: 1911-1918, 1993; *DNA Cell Biol.* 10: 525-536, 1991; Groupp et al. *J. Biol. Chem.* 269: 22178-22187, 1994). α-fetoprotein gene expression was regulated not only via a promoter, but also an enhancer. The enhancer, a cis-acting transcriptional regulatory element, is typically characterized by its ability to augment transcription over a long distance and relatively independently of orientation and position with respect to its respective gene to be acted on.

Some studies have been showed that the 5' flanking region of the human AFP gene contains transcription regulatory elements with characteristics of enhancers (Watanabe et al. J. Biol. Chem. 262: 4812-4818, 1987; CA. Pat. Appl. No. 2,134, 994).

In the study of Watanabe et al. (*J. Biol. Chem.* 262: 4812-4818, 1987), they examined a cis-acting regulatory function associated with the upstream region of the human AFP gene by assaying transient expression of the CAT gene supported by the AFP 5-flanking sequence. These result indicated that the region between −5.1 and −2.9 kb of the AFP 5' flanking sequence is important for the enhancement of CAT expression in HuH-7 hepatoma cells. These result also showed a 7.5 kb fragment and a 0.4 kb fragment from −3.7 to −3.3 kb of the AFP 5' flanking sequence were both exhibiting cell specificity.

According to the report of Yoshitake Hayashi et al. (*J. Biol. Chem.* 267: 14580-14585, 1992) and the disclosure of US Pat. Pub. No. 2003/0017139, the −1789 to −1773 by human albumin 5 flanking exhibited enhancer activity as well as liver cell specificity. Based on the experimental result of the present invention, however, a $pALB_{2.0}$ fragment (−1954/+39 bp) comprising the above-mentioned sequence exhibits stimulatory activity in hepatoma and nonhepatic cells, indicating that $pALB_{2.0}$ fragment has lack of liver cell specificity. Therefore, it is unable to predict that the ability of liver cell specificity can still remain in different length of a known sequence with liver cell specificity. Therefore, there are few application researches about sequences with liver cell specificity.

SUMMARY OF THE INVENTION

The present invention relates to a chimeric regulatory sequence with liver cell specificity that encodes a nucleotide sequence shown in SEQ ID NO: 1. The regulatory sequence comprises a proximal regulatory sequence (−1903/+43 bp) and a distal enhancer sequence (−5.2/−2.9 kb) of the human α-fetoprotein gene.

The regulatory sequence can be operably linked to a heterologous polynucleotide to effect transcriptional control of the linked gene.

The present invention further includes a method for purifying liver cells from a heterogeneous population of cells, comprising: transfecting the cells, a DNA encoding a selectable marker under a regulatory sequence that is specifically active in liver cells; separating those cells expressing the selectable marker from cells not expressing the marker; and obtaining purified liver cells.

The present invention further includes a method for purifying hepatic progenitor cells from the partially differentiated HES cells. The method comprises the steps of: (a) dissociating a 7-day-old embryoid body into a plurality of single cells; (b) transfecting the cells with a DNA fragment encoding a regulatory sequence that is specifically active in hepatic-lineage cells, wherein the regulatory sequence comprises partial sequence of the human a-fetoprotein gene; and (c) obtaining a-fetoprotein-expressing hepatic progenitor cells.

The regulatory sequence is a nucleotide sequence shown in SEQ ID NO: 1.

The DNA fragment encoding a regulatory sequence of the present invention is further comprising at least one selectable marker. The marker may be a fluorescent marker or an antibiotic resistance protein. The fluorescent protein may be any of green fluorescent protein, lacZ, firefly Rennila protein, luciferase, red, yellow, and blue cyan proteins. The cells containing the marker may be seperated from the cells lacking the marker using a fluorescent activated cell sorter or a laser scanning cytometer. Where the selectable marker is an antibiotic resistance marker, for example, hygromycin, neomycin, zeocin and puromycin, separating cells expressing the marker from those that cannot express can be achieved by culturing the cells in a selective medium containing antibiotics.

Accordingly, introducing polynucleotides into cells may be facilitated by formulations that include a cationic lipid reagent, a cationic non-lipid polymer transfection reagent, a liposomal transfection reagent for introducing into the population of cells. Alternatively, electroporation may be used.

Other objects, advantages, and novel features of the invention will become more apparent from the following detailed description when taken in conjunction with the accompanying drawings.

BRIEF DESCRIPTION OF THE DRAWINGS

The foregoing features of embodiments of the invention will be more readily understood by reference to the following detailed description, taken with reference to the accompanying drawings, in which.

DETAILED DESCRIPTION OF THE PREFERRED EMBODIMENT

Definitions

Figure 1:
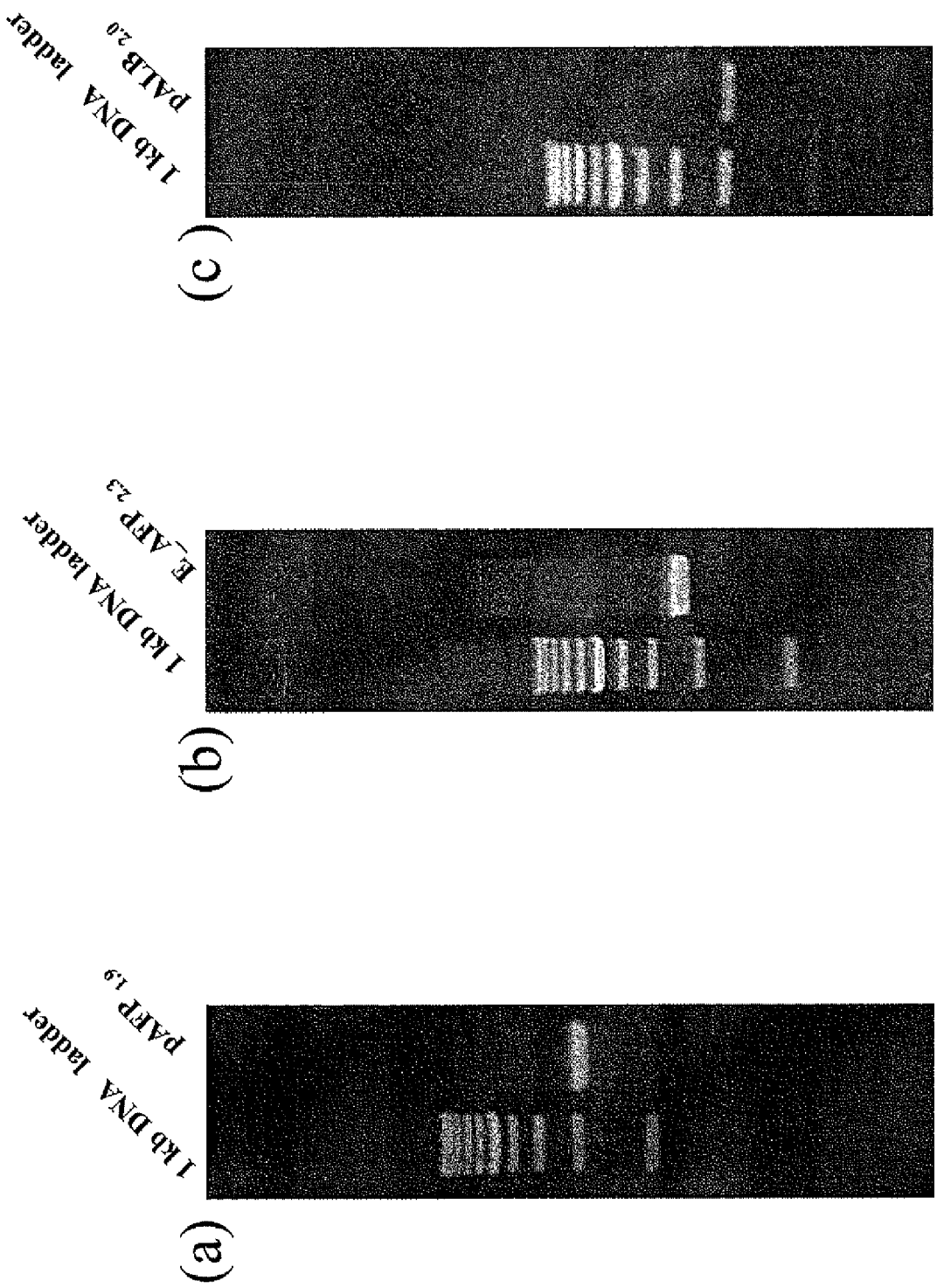
FIGS. 1(a)-1(c) are the electrophoresis results of the amplified products of the sequence fragments $pAFP_{1.9}$ (FIG. 1(a)), $E\_AFP_{2.3}$ (FIG. 1(b)) and $pALB_{2.0}$ (FIG. 1(c)).

As used in this description and the accompanying claims, the following terms shall have the meanings indicated, unless the context otherwise requires:

The term himeric means two nucleotide sequences that are linked together to form a new one.

The term "regulatory sequence" refers to a nucleic acid sequence capable of controlling the transcription of an operably associated gene. A regulatory sequence of the invention may include a promoter and/or an enhancer, for example. Therefore, placing a gene under the regulatory control of a promoter or a regulatory element means positioning the gene such that the expression of the gene is controlled by the regulatory sequence(s). In general, promoters are found positioned 5' (upstream) of the genes that they control. Thus, in the construction of promoter-gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates. Enhancers are believed to be relatively position and orientation independent in contrast to promoter elements.

The term "markers" means DNA, RNA or protein that can be readily detected in cells and provide a means of distinguishing those cells containing the marker from those that lack the marker. Markers can be used to track cellular events in circumstances involving a changing environment. Markers can be intrinsic in the cells of interest or may be foreign and introduced into the cells to express proteins. For example, where foreign DNA encodes markers, these are sometimes called reporter genes. "Reporter genes" are those genes that "report" the presence of particular cells and may include cell specific enhancers and promoters that control whether tissue specific expression of a gene occurs and how it is modulated. Reporter genes may be introduced into cells by transfection.

Transfection of cells with genes encoding reporter proteins provides a means for tracking cells. Examples of reporter genes include green fluorescent protein, Lac Z, firefly Rennila protein, red, yellow or blue cyan fluorescent proteins or other fluorescent protein, including those found in marine animals. Other markers include antibiotic resistance proteins to protect cells against, for example, neomycin, hygromycin, zeocine and puromycin.

The term ransfection means the introduction of nucleic acid into cells. Transfection may occur in vivo as well as in vitro. The methods comprise: electroporation, lipofection, calcium phosphate precipitation, DEAE-dextran transfection and so on.

We have established herein methods for genetically engineering liver cells and we describe an efficient protocol for transfecting these cells. By introducing genetic modifications into cells, we can manipulate these cells in vitro, we can purify liver cells using selectable markers and we can use, track, manipulate them.

Markers can be used to isolate specific cell types from a heterogeneous culture.

For example, when a population of cells is transfected with a DNA containing a gene that codes for a drug resistance protein driven by a tissue specific promoter, the only cell which will survive in the presence of the drug is the cell type capable of expressing the drug resistance gene.

Embodiment 1

Synthesis of the Chimeric Regulatory Sequence Fragment

Human genomic DNA is extracted from bone marrow mesenchymal stem cells and served as a template for amplification by polymerase chain reaction (PCR). The proximal regulatory sequence (including promoter, −1903/+43 bp) in 5' flanking region of human α-fetoprotein gene is amplified and named $pAFP_{1.9}$. The distal enhancer sequence (−5.2/−2.9 kb) in 5' flanking region of human α-fetoprotein gene is amplified and named $E\_AFP_{2.3}$. The proximal regulatory sequence in 5' flanking region (−1954/+39 bp) of human albumin gene, a control group of liver cell specific sequence, is amplified and named $pALB_{2.0}$. The primer sequences used are listed in Table 1, and the reaction condition are 94 for 4 min; 10 cycles of 94 for 1 min, 60 for 1 min, and 72 for 5 min; 25 cycles of 94° C. for 1 min, 56° C. for 1 min, and 72° C. for 5 min; then 56 for 1 min; 72 for 7 min; and finally maintained at 25.

The PCR products are determined by electrophoresis, and the results are shown as FIG. 1(a) proximal regulatory sequence in 5' flanking region of human α-fetoprotein gene, FIG. 1(b) distal enhancer sequence in 5' flanking region of human α-fetoprotein gene, and FIG. 1(c) proximal regulatory sequence in 5' flanking region of human albumin gene.

TABLE 1

| Names of amplified sequence | Sequence location | Primer sequence | Product size (kb) |
|---|---|---|---|
| $pAFP_{1.9}$ | −1903 to +43(bp) | Fw: AFP_P_S: SEQ ID NO. 2<br>Re: AFP_P_A: SEQ ID NO. 3 | 1960 |
| $E\_AFP_{2.3}$ | −5.2 to .9(kb) | Fw: AFP_E2.2S: SEQ ID NO. 4<br>Re: AFP_E2.2A: SEQ ID NO. 5 | 2288 |
| $pALB_{2.0}$ | −1954 to +39(bp) | Fw: ALB_P_S: SEQ ID NO. 6<br>Re: ALB_P_A: SEQ ID NO. 7 | 2009 |

The above synthesized pAFP$_{1.9}$ and E_AFP$_{2.3}$ are digested with restriction enzymes Xho I and Sac I, respectively. T4 DNA ligase (purchased from BioLab NEB) is used to ligate the two digested fragments, and the length of resulted chimeric sequence is 4239 bp, which is named E_pAFP4.2, as shown in SEQ ID NO: 1.

Embodiment 2

Test of Liver Cell Specific Activity of the Chimeric Regulatory Sequence Fragment The above mentioned fragments pAFP1.9, E_pAFP4.2 and pALB2.0 are integrated into the luciferase expression vector (pGL2-B, Promega) and the enhanced green fluorescence protein (EGFP) expression vector (pEGFP-1, BD, Clontech) for plasmid construction separately. The prepared constructs encoding reporter genes include: pAFP$_{1.9}$/GL2-B, E_pAFP$_{4.2}$/GL2-B, pALB$_{2.0}$/GL2-B, pAFP$_{1.9}$/EGFP, E_pAFP$_{4.2}$/EGFP and pALB$_{2.0}$/EGFP.

The above-mentioned constructs are purified in large scale for the use of transfection into human hepatoma (HuH-7, HepG2-C3A) and non-hepatoma (H1299, 293T) cell lines, and the expression of luciferase activity and enhanced green fluorescence protein are recorded.

The luciferase activity is measured with the following steps: 1-2 $10^5$ cells are seeded in a 6-well culture dish for 16-18 hours before transfection performs. 1 μg of constructed reporter gene plasmid mentioned above is mixed with 0.4 μg of pRC/CMV-β (internal control). An efficient amount of Lipofectamine™ (Invitrogen) is added and the transfection is performed according to the instruction. After 48 hours, 200 μl of cell extract is collected for measuring luciferase activity. In brief, 20 μl of cell extract is mixed with Luciferase Assay System Kit™ (Promega), and then read the absorption value in the luminometer (Turner BioSystems TD20/20) to determine the activity of luciferase. The reading program is set as delay time for 2 seconds and integration time for 10 seconds. Moreover, 50 μl of the cell extract is mixed with β-Galactosidase Enzyme Assay Kit™ (Promega), and o-nitrophenol developing value is read under 420 nm as an internal control. The resulting luminescence of reporter gene is corrected with o-nitrophenol developing value to obtain a relative luciferase activity of the above regulatory sequence.

Analysis of the expression of enhanced green fluorescence protein is as following: to begin with, 1 μg of above-mentioned reporter gene plasmid is mixed with 2 μl of Lipofectamine™. After incubation for 45 min, cells cultured in the 6-well dish are performed in transfection for 3 hrs. After 48 hours, the expression of enhanced green fluorescence protein is observed directly by using a fluorescence microscope (480-525 nm fluorescence filter is used).

Embodiment 3

Purification of Liver Cells from a Heterogeneous Population of Cells

The chimeric regulatory sequence E_pAFP$_{4.2}$ of human α-fetoprotein gene is used to purify liver cells from a heterogeneous population of cells. First, $5 \times 10^6$ of HuH-7 hepatoma cells and H1299 lung cancer cells are seeded in the 10-cm culture dishes, respectively. 8 μg of E_pAFP$_{4.2}$/EGFP plasmid DNA is mixed with 32 μl of Lipofectamine 2000™ (Invitrogen), and the total volume of medium is adjusted to 1000 μl with OPTI-MEM (Invitrogen). After incubation at room temperature for 20 minutes, 500 μl of each is added in the PBS-washed culture dish. The medium volume in each culture dish is further filled to 2 ml with serum-conditioned media, and the culture dishes are transferred to an incubator for 24 hours in transfection.

The cells are washed with PBS and refilled with 5 ml culture medium for another 24 hours incubation. The cells transfected for 48 hours are digested and collected with trypsin-EDTA, and then centrifuged at 1000 rpm. The waste is removed, and then the fresh serum-contained medium is added. To prepare a control group herein with untransfected cells, the preparation is identical to the transfected cells mentioned above except the addition of the plasmid DNA.

To obtain the standard fluorescence distribution of the single cell type, $1 \times 10^4$ cells of above transfected or untransfected HuH-7 cells and H1299 cells are collected and analyzed in the FACSVantage SE flow cytometer (Becton Dickinson company). For cell sorting, transfected HuH-7 and H1299 cells in an equal ratio are mixed, in which the total cells are $2 \times 10^6$, and individual cell types are separated according to fluorescence expression by the FACSVantage SE flow cytometer. The excitation light source is a 488 nm wavelength of laser beam to detect the intensity of enhanced green fluorescence protein. The sorting rate is set in 2,000 cells/sec.

Embodiment 4

Immuno-Staining of Purified Cells

The sorted cells from Embodiment 3 are processed in immuno-staining to detect the expression of human a-fetoprotein in enhanced green fluorescence protein-positive (EGFP$^+$) cells. After transferring these cells on the chamber slide for 24 hours incubation, the media is removed. The cells are washed in PBS for three times, and fixed with 4% paraformaldehyde at room temperature for 15 min. Further, the cells are reacting with 0.1% triton X-100 for 2-3 times, and then blocking with 10% normal goat serum for 2 hours. The cells are incubated with the first antibody, rabbit anti-human α-fetoprotein (Dako company), for 1 hour at room temperature. Then the cells are reacted with the second antibody, FITC goat anti-rabbit IgG conjugate (Zymed company), for another 1 hour at room temperature. Finally, the cells are embedded with embedding solution and observed under the fluorescence microscope.

Embodiment 5

Determination of Liver Cell Specificity

Figure 2:
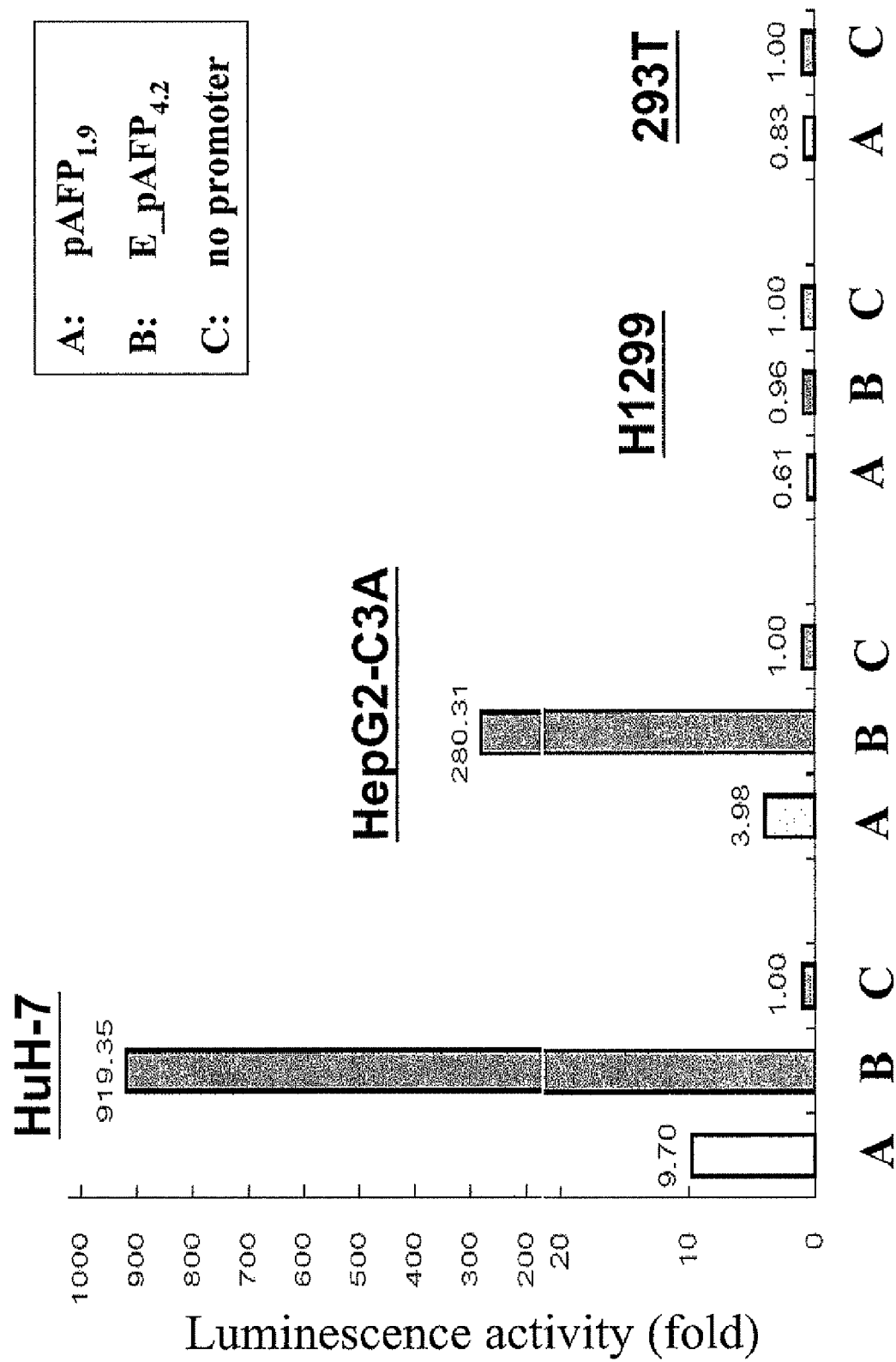
FIG. 2 is the liver cell specificity presented with luminescence activity in Embodiment 2 of the present invention.

In Embodiment 2, the liver cancer (HuH-7 and HepG2-C3A) and non-liver cancer (H1299 and 293T) cell lines are transfected with pAFP$_{1.9}$/GL2-B or E_pAFP$_{4.2}$/GL2-B plasmid DNA, respectively. The luciferase activities are measured for the activation of these regulatory sequences. The results are shown in FIG. 2. The activity of pAFP$_{1.9}$ regulatory sequence is 9.7-fold and 3.98-fold higher than that of promoterless sequence (GL2-B vector only) in the liver cancer cell lines HuH-7 and HepG2-C3A, respectively. In the non-liver cancer cell lines H1299 (non-small cell lung cancer cell) and 293T (kidney epidermal cell), the activity are 0.61 and 0.83-fold compared to the promoterless sequence, separately. The results indicate that pAFP$_{1.9}$ regulatory sequence exhibits an activity merely in the liver cancer cell lines, namely for liver cell specificity.

In the liver cancer cell lines HuH-7 and HepG2-C3A, the activities of E_pAFP$_{4.2}$ regulatory sequence are 919.35 and 280.31-fold higher than that of promoterless sequence (GL2-B vector only), respectively. In the non-liver cancer cell lines H1299, the activity is 0.96-fold compared to the promoterless sequence. It is indicated that E_pAFP$_{4.2}$ regulatory sequence exhibits an activity merely in the liver cancer cell lines, namely for liver cell specificity. Moreover, the intensity of transcriptional activation by E_pAFP$_{4.2}$ regulatory sequence is about 70-90 folds higher than that of pAFP$_{1.9}$ regulatory sequence, indicating that the chimeric regulatory sequence could enhance the activity and function in a liver cell.

Figure 3:
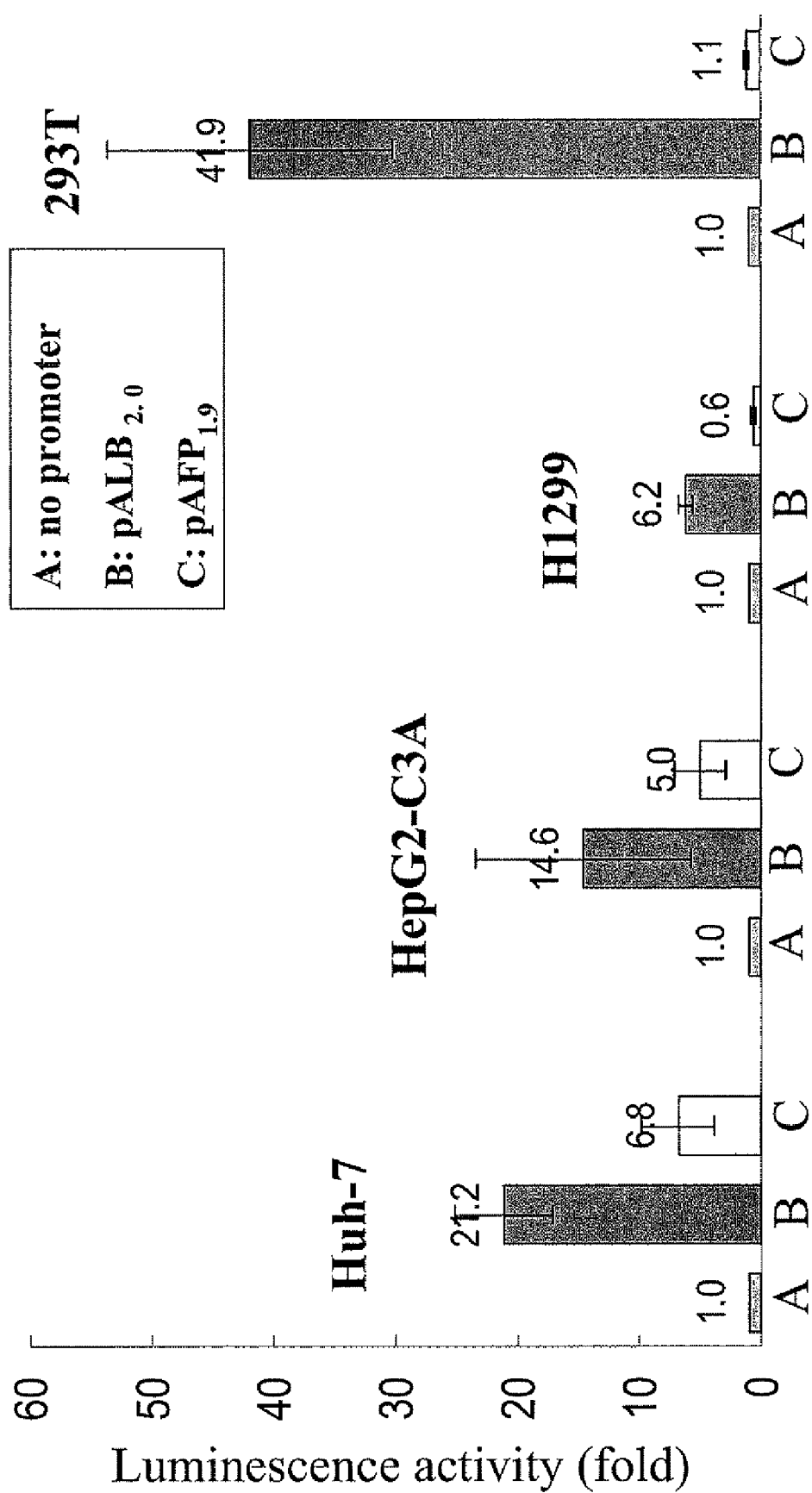
FIG. 3 is the luminescence activity the regulatory sequence of albumin gene without liver cell specificity in Embodiment 2 of the present invention.

Further, the liver cancer (HuH-7 and HepG2-C3A) and non-liver cancer (H1299 and 293T) cell lines are transfected with pAFP$_{1.9}$/GL2-B or pALB$_{2.0}$/GL2-B plasmid DNA, respectively. The luminescence activities are measured of these regulatory sequences for the determination of gene transcription. The results are shown in FIG. 3. In the liver cancer cell lines HuH-7 and HepG2-C3A, the activities of pAFP$_{1.9}$ regulatory sequence are 6.8 and 5.0-fold higher is than that of promoterless sequence, respectively. In the non-liver cancer cell lines H1299 and 293T, the activities are 0.6 and 1.1-fold higher than that of promoterless sequence. It is indicated that pAFP$_{1.9}$ regulatory sequence exhibits an activity merely in the liver cancer cell lines, namely for liver cell specificity. However, in the liver cancer cell lines HuH-7 and HepG2-C3A, the activities of pALB$_{2.0}$ regulatory sequence are 21.2 and 14.6-fold higher than that of promoterless sequence, respectively. In the non-liver cancer cell lines H1299 and 293T, the activities are 6.2 and 41.9-fold higher than that of promoterless sequence, respectively. It is indicated that pALB$_{2.0}$ regulatory sequence exhibits relatively high activity both in the liver cancer and non-liver cancer cell lines, meaning no liver cell specificity being observed.

Figure 4:
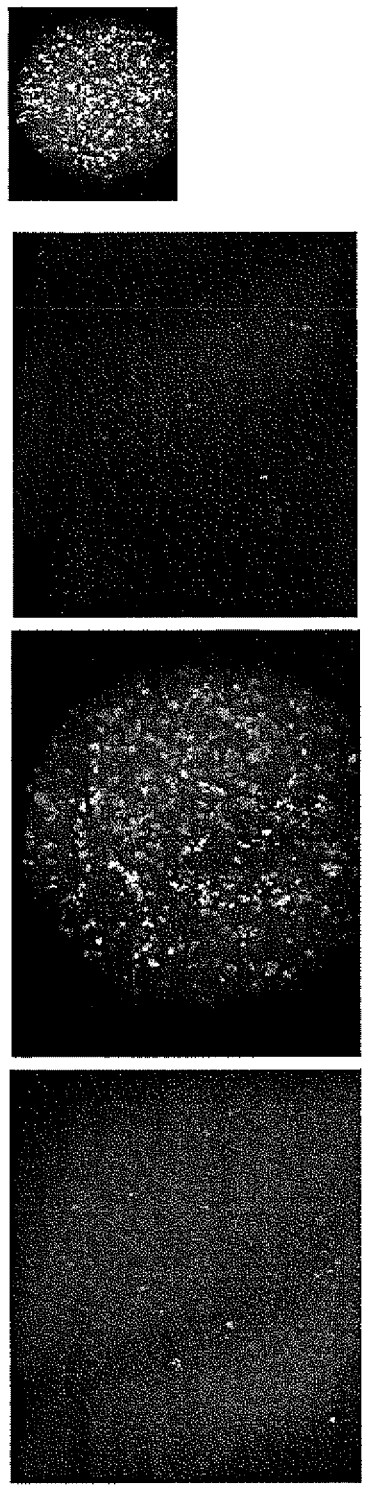
FIG. 4 is the green fluorescent activity for liver cell specificity in Embodiment 2 of the present invention.
Figure 4:
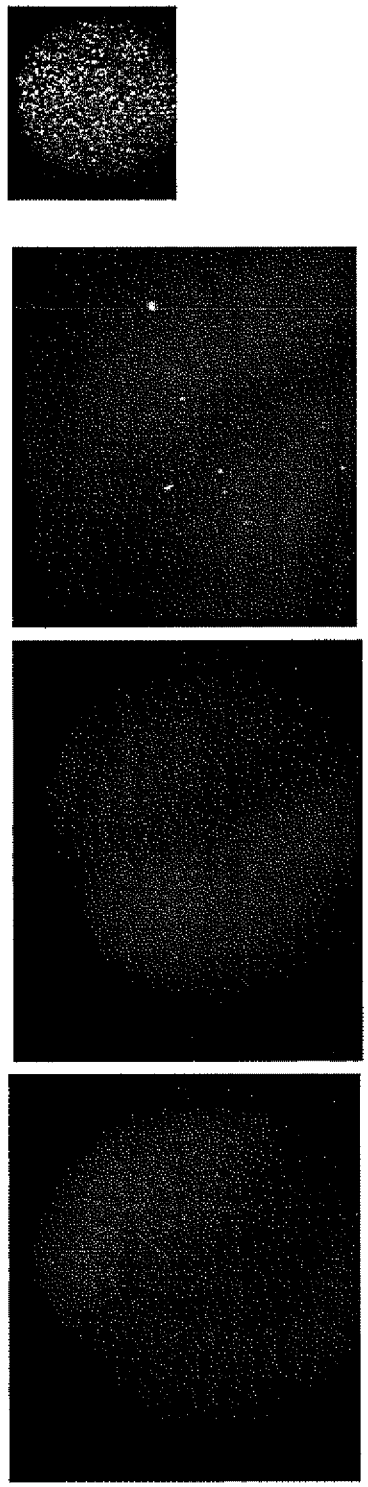

The liver cell specific activities among pAFP$_{1.9}$, E_pAFP$_{4.2}$ and pALB$_{2.0}$ regulatory sequences are also determined by expression of enhanced green fluorescence protein. The results are shown in FIG. 4. pAFP$_{1.9}$ and E_pAFP$_{4.2}$ regulatory sequences could merely trigger the expression of enhanced green fluorescence protein in the liver cancer cell line. However, pALB$_{2.0}$ regulatory sequence triggers the expression of the enhanced green fluorescence protein both in the liver cancer and non-liver cancer cell lines. The results are identical to the above-mentioned luminescence activity. The regulatory sequences of pAFP$_{1.9}$ and E_pAFP$_{4.2}$, but not pALB$_{2.0}$, do exhibit liver cell specificities (the pgk result in the right panel of FIG. 4 is as the positive control).

However, based on the report from Yoshitake Hayashi et al. (*J. Biol. Chem.* 267:14580-14585, 1992) and the disclosure of US Patent No. 2003/017139, the 5' flanking region begins from −1789 to −1773 by of human albumin gene was not only an enhancer, but also exhibited liver cell specificity. According to the experiment result of the present invention, however, a pALB$_{2.0}$ (−1954/+39 bp) fragment carrying the above-mentioned regulatory sequence does not have liver cell specificity. Therefore, on the basis of the known sequence with liver cell specificity, it is unable to predict that the ability of liver specificity can still remain in different length of a known sequence with liver cell specificity.

However, in the document of Watanabe et al. (*J. Biol. Chem.* 262: 4812-4818, 1987), though it was evidenced that a 7.5 kb fragment and a 0.4 kb fragment (−3.7/−3.3 kb) in 5' flanking region of human AFP gene were both exhibiting cell specificity, the author did not mention the specificity of the other sequences therein. Although the disclosed sequence in the present invention is similar to the documented sequence pAF$_{5.1}$[Δ1] in this document of Watanabe et al., it is unable to predict the liver specificity of the present sequence by a person skilled in the art. pAF$_{5.1}$[Δ1] is a sequence with 1 kb deletion of the 5.1 kb fragment in 5' flanking region of human AFP gene (i.e. including the proximal regulatory sequence −1.9 kb/+29 by and distal regulatory sequence −5.1/−2.9 kb in the 5' flanking region of human α-fetoprotein gene).

In Embodiment 3, the E_pAFP$_{4.2}$ chimeric regulatory sequence from the Embodiment 1 is further used to examine the application for cell sorting. The function of liver cell specificity is further applied in purification of liver cells from a heterogeneous population of cells.

Figure 5:
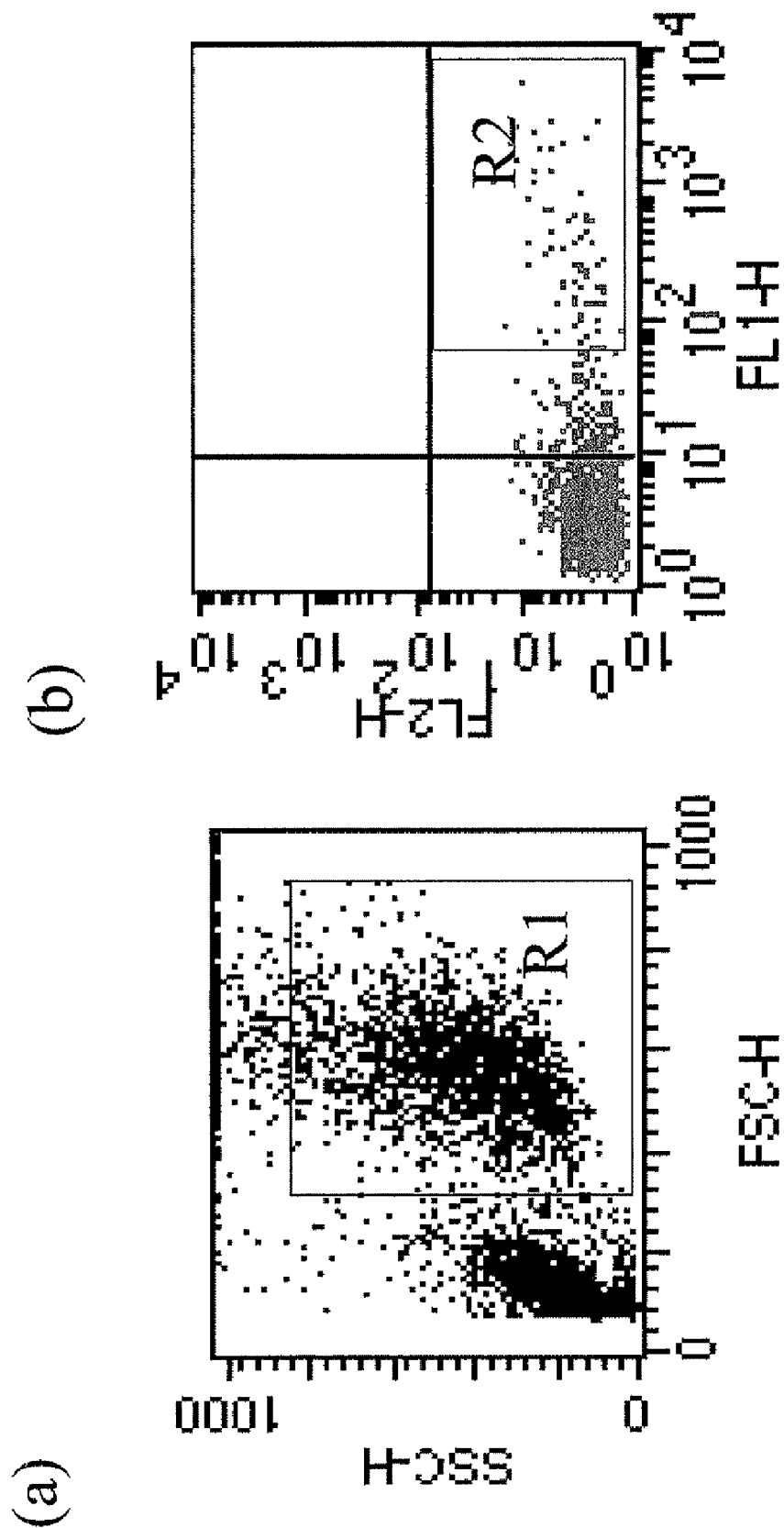
FIGS. 5(a)-(b) are the results of cell mass purification by flow cytometer in Embodiment 3 of the present invention.

For cell sorting, an equal ratio of H1299 and HuH-7 cells transfected with E_pAFP$_{4.2}$/EGFP plasmid DNA are mixed to identify the expression of the enhanced green fluorescence protein by using a FACSVantage SE flow cytometer. In FIG. 5(a), the cells in R1 area (alive cells) are collected for cell sorting. R2 area in FIG. 5(b) represents the cells collected based on the intensity of green fluorescence.

Figure 6:
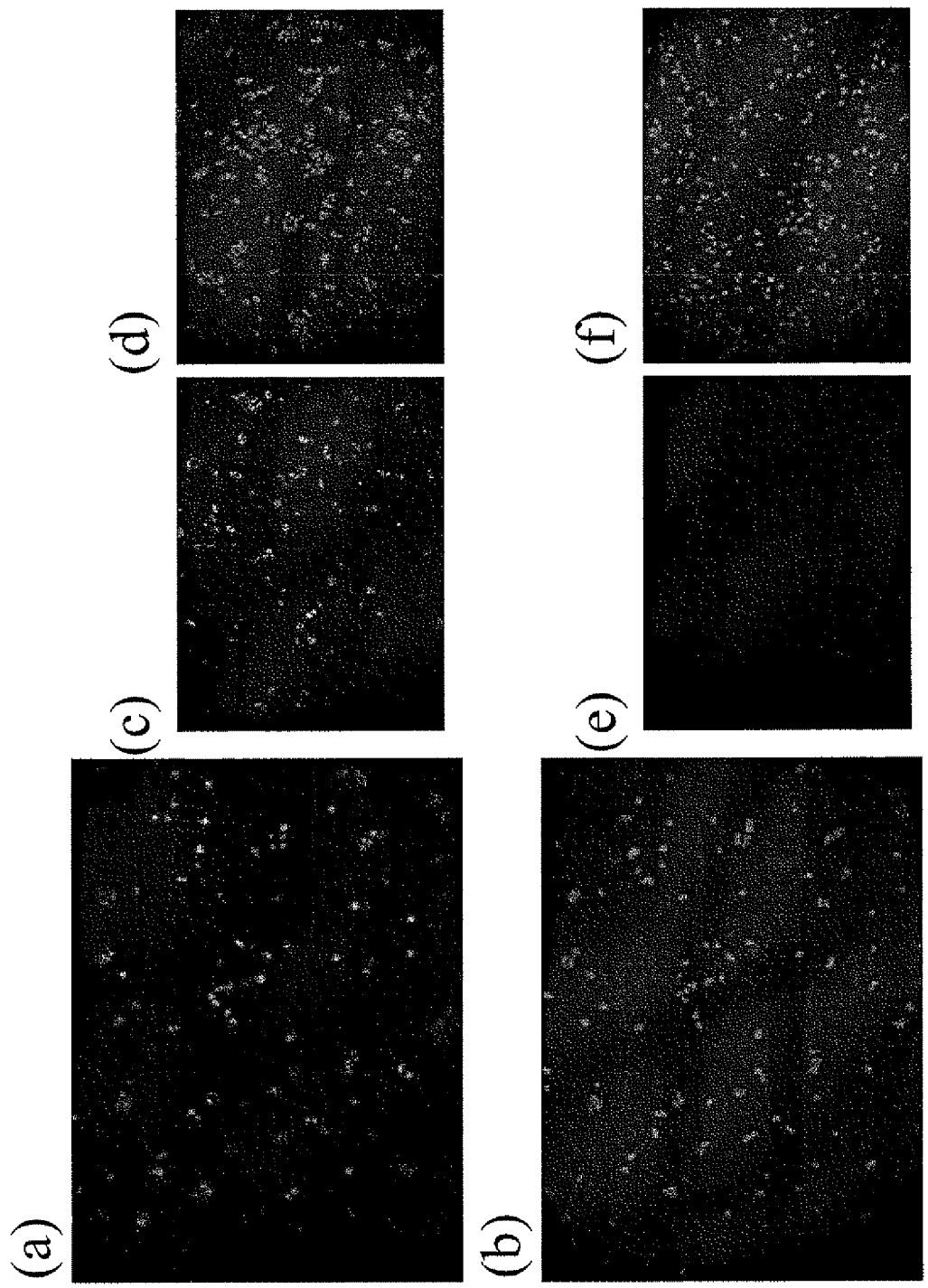
FIGS. 6(a)-(f) are the results of immuno-staining in Embodiment 4 of the present invention

To characterize the sorted EGFP$^+$ cells being the HuH-7 liver cells, the cells from R2 are processed in immuno staining described in Embodiment 4. The results are shown in FIGS. 6 (a) and (b), α-fetoprotein was expressed in all the isolated EGFP$^+$ cells, meaning that these cells are HuH-7 (liver cell), and there are no H1299 (non-liver cell) cells existed. Therefore, the E_pAFP$_{4.2}$ chimeric regulatory sequence is capable of applying in purification of liver cells from a heterogeneous population of cells. FIGS. 6 (a) and (b) are both EGFP$^+$ cells (from R2 area of FIG. 5) after sorting by the FACSVantage SE flow cytometer, (c) and (d) are both HuH-7 cells as a positive control, (e) and (f) are both H1299 cells as a negative control, wherein (a), (c) and (e) are all immuno-stained with anti-human AFP antibody, and (b), (d) and (f) are the nucleus staining results with DAPI.

Embodiment 6

Purification of α-Fetoprotein Expressing Cells from HES Cells

The chimeric regulatory sequence E_pAFP$_{4.2}$ of human α-fetoprotein gene is used to purify the α-fetoprotein expressing cells from the HES cells. The HES cells can be utilized with undifferentiated cells or partially differentiated cells such as embryoid bodies (EBs), or embryonic stem (ES) cells. Furthermore, the partially differentiated cells are preferably 7~14 day-old cells.

The HES cells (HES3 cell line from ESI in Astralia is used in the present embodiment) are cultured in HES culture medium and the mouse embryonic fibroblasts are used as feeder cells to maintain the HES cells undifferentiated.

After seven days culturing, the HES cell clusters are dissociated into several smaller clusters. The smaller clusters are used to form embryonic bodies by hanging-drop method. Each small cluster is cultured with 35-40 µl medium in the top plate of a petri-dish, and the top plate is up-side-down to cover the bottom plate having 10 ml sterile water to maintain the humidity in the culture. The embryoid bodies are formed in HES medium under the gravity force. Change the culture medium for each 3-4 days.

Figure 7:
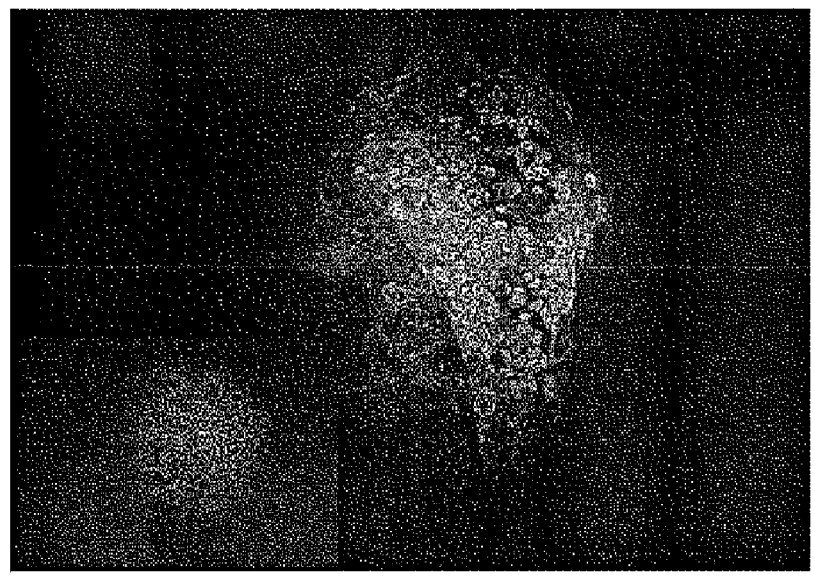
FIG. 7 shows the result of immunostaining in Embodiment 6. Immunostained AFP-positive cells were localized together as clusters in a culture of 7-day-old EBs followed an additional 7 days in a monolayer. Larger figure: AFP staining. Inset: DAPI staining for nuclei.

After another seven days culturing, the formed embryonic bodies (EBs) are harvested and seeded in a culture plate. The seeded EBs are attached on the culture plate, and AFP(+) cells are spontaneously differentiated from the EBs, and the aggregated AFP(+) cells are as shown in FIG. 7. FIG. 7 illustrates the immunostained AFP(+) cells in a culture of 7-day-old EBs followed an additional 7 days culturing in a monolayer. These AFP(+) cells are mostly localized together as clusters.

Figure 8:
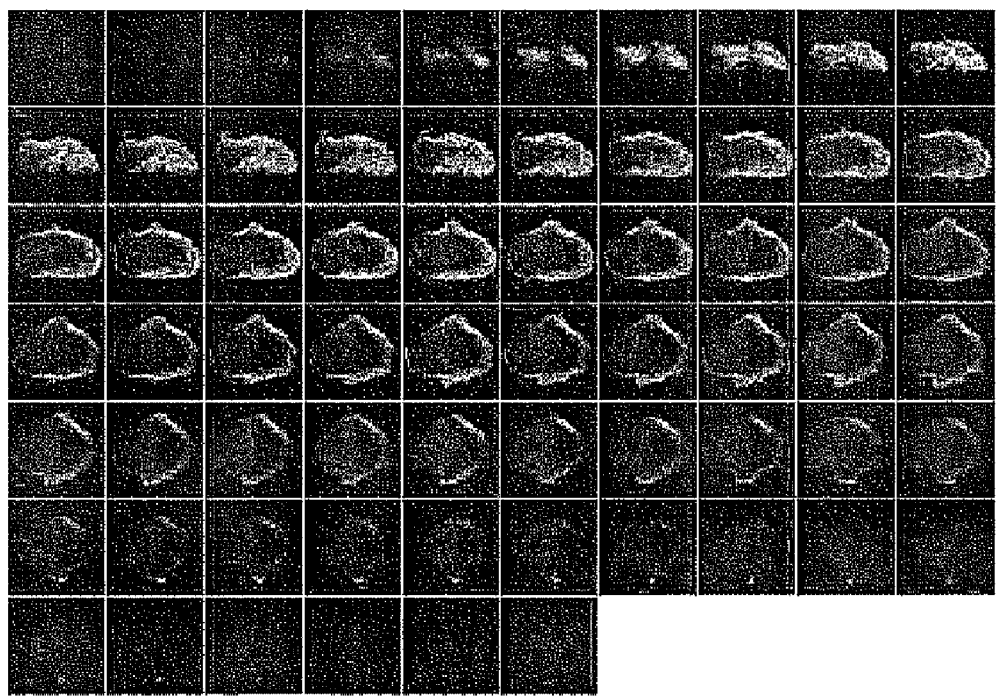
FIG. 8 shows the result that the spatial distribution of immunostained AFP-positive cells in 7-day-old EBs is analyzed by confocal microscope. Light grey: AFP staining, dark grey: PI staining for nuclei.

In order to locate the spatial distribution of immunostained AFP(+) cells in EBs, the immunohistochemical staining of 7-day-old EBs is carried out and the expression pattern is analyzed by confocal microscope. As shown in serial sections analyzed by confocal microscope, the immunostained AFP$^+$ cells are located in the outer layer of 7-day-old EBs. (FIG. 8). This phenomenon may reflect the mechanism of endoderm cells spatial distribution during HES cells differentiation. In vitro, when ES cells had developed into EBs, endodermal cells including hepatocytes, were situated at the outside of the EBs. As embryonic development in vivo, these endoderm-derived hepatocytes would shift inside of the embryo.

The isolation of a specific population of cells from a heterogeneous culture of differentiating HES cells is necessary for cellular transplantation. The differentiated HES cells can eliminate the tumorgenic potential of ES cells, which is useful in therapeutic medicine. As demonstrated above, the immunostained AFP(+) cells appeared to exist in the outer layer of 7-day-old EBs, therefore, the chimeric promoter with liver specific activity of the present invention is useful to isolate these hepatic lineage cells.

Figure 9:
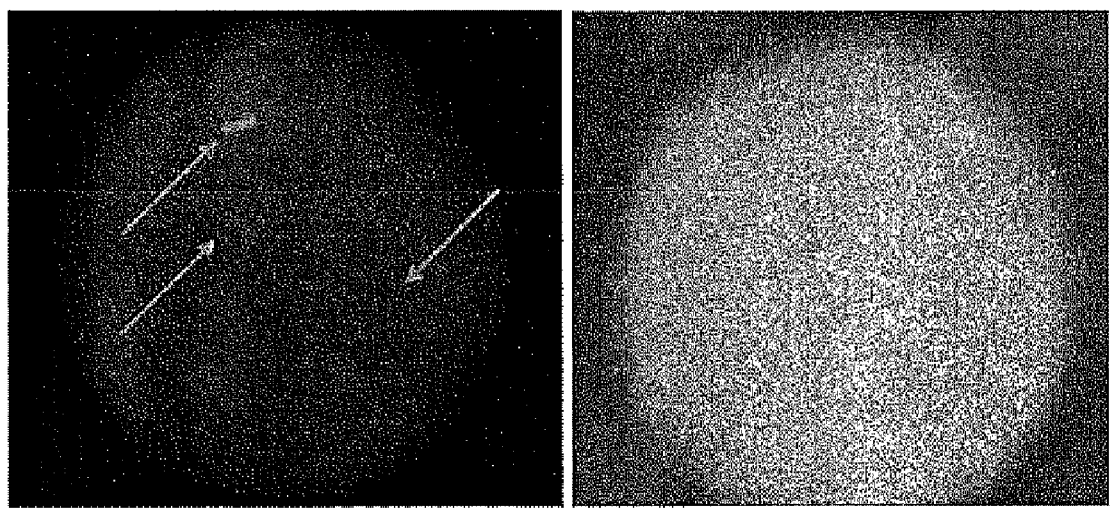
FIG. 9 shows the AFP-positive cells in 7-day-old EBs could be labeled by E_pAFP4.2-eGFP expression plasmids. Left: fluorescence image, right: light field.

The formed EBs (or ES) can be transfected with the chimeric regulatory sequence (SEQ ID NO:1) in the forms of clusters or multiple single cells. However, to achieve a better transfection efficiency, the cells used for transfection in the present embodiment are single cells. Therefore, the 7-day-old EBs are dissociated into single cells first, which are then transfected with the chimeric regulatory element-E_pAFP$_{4.2}$ and plated on the culture dish. By using eGFP as a reporter, the chimeric regulatory element-E_pAFP$_{4.2}$ can isolate the hepatic lineage cells from 7-day-old EBs. As demonstrated in FIG. 9, some of the 7-day-old EBs cell population could be marked by eGFP expression.

It is important to verify that the fluorescent cells actually express liver markers. As results demonstrated above (FIGS. 6 (a) and 6 (b)), all eGFP$^+$ cells sorted from mixed types of cells through E_DAFP$_{4.2}$ sequence expressed AFP liver marker. With the description herein, the hepatic-like cells could be efficiently isolated from differentiating HES cells by a liver-specific regulatory element. Although the present invention has been explained in relation to its preferred embodiment, it is to be understood that many other possible modifications and variations can be made without departing from the spirit and scope of the invention as hereinafter claimed.

What is claimed is:

1. A method for purifying hepatoma cells from a heterogeneous population of cells, comprising the steps of:
   (a) transfecting the heterogeneous population of cells with a DNA fragment encoding a selectable marker under the control of a regulatory sequence comprising the nucleotide sequence of SEQ ID NO:1, and that is specifically activated in hepatoma cells;
   (b) separating those cells expressing the selectable marker from the population of cells; and
   (c) obtaining purified hepatoma cells.

2. The method as claimed in claim 1, wherein the regulatory sequence consists of the nucleotide sequence of SEQ ID NO:1.

3. The method according to claim 1, wherein the selectable marker is a fluorescent marker.

4. The method as claimed in claim 3, wherein the fluorescent marker is selected from the group consisting of green fluorescent protein, lacZ, luciferase, red fluorescent protein, cyan fluorescent protein and yellow fluorescent protein.

5. The method as claimed in claim 3, wherein the fluorescent marker is enhanced green fluorescent protein.

6. The method as claimed in claim 1, wherein (b) further comprises separating the cells containing the marker from the population of cells using a fluorescent activated cell sorter or a laser scanning cytometer.

7. The method as claimed in claim 1, wherein the selectable marker is an antibiotic resistance marker.

8. The method as claimed in claim 1, wherein step (b) further comprises separating cells by culturing the cells in a selective medium containing antibiotics.

9. The method as claimed in claim 1, wherein the cells are transfected by lipofection.

10. The method as claimed in claim 1, wherein the method further comprises a step (d) after step (c), identifying said purified cells with an immunostaining method.

11. The method as claimed in claim 10, wherein said immunostaining method in step (d) is used to examine the α-fetoprotein expression in the purified cells.

12. A method for purifying α-fetoprotein expressing cells from Human Embryonic Stem Cells (HES) cells, comprising the steps of:
   (a) obtaining undifferentiated HES cells;
   (b) transfecting the HES cells with a DNA fragment encoding a selectable marker under the control of a regulatory sequence, wherein the regulatory sequence comprises the nucleotide sequence of SEQ ID NO:1;
   (c) differentiating the undifferentiated HES cells and selecting those differentiated HES cells expressing the selectable marker; and
   (d) obtaining cells that express α-fetoprotein.

13. The method according to claim 12, wherein the α-fetoprotein expressing cells are endoderm cells.

14. The method according to claim 12, wherein the α-fetoprotein expressing cells are hepatic progenitor cells.

15. The method according to claim 12, wherein the selectable marker is a fluorescent marker.

16. The method as claimed in claim 15, wherein the fluorescent marker is selected from the group consisting of green fluorescent protein, lacZ, luciferase, red fluorescent protein, cyan fluorescent protein and yellow fluorescent protein.

17. The method as claimed in claim 15, wherein the fluorescent marker is enhanced green fluorescent protein.

18. The method according to claim 12, wherein the HES cells are transfected by lipofection.

19. The method as claimed in claim 12, wherein the method further comprises a step (e) after step (d), identifying said obtained cells with an immunostaining method.

20. The method as claimed in claim 12, wherein the regulatory sequence consists of the nucleotide sequence of SEQ ID No:1.

* * * * *

SEQUENCE LISTING

<160> NUMBER OF SEQ ID NOS: 7

<210> SEQ ID NO 1
<211> LENGTH: 4239
<212> TYPE: DNA
<213> ORGANISM: Homo sapiens

<400> SEQUENCE: 1

```
gtccctgcag cccctatcac tgaattctta gaaatatggg ggtaggggtg gtggtggtaa      60
ttctgttttc tccccatagg tgagataagc attgggttaa atgtgctttc tctctctccc     120
tctcctttct taagaattaa gggacagact atgggctgga ggactttgag gatgtctgtc     180
tcataacact tgggttgtat ctgttctatg gggcttgttt taagcttggc aacttgcaac     240
agggttcact gactttctcc ccaggcccaa ggtactgtcc tcttttcata tctgttttgg     300
ggcctctggg gcttgaatat ctgagaaaat ataaacattt caataatgtt ctgtggtgag     360
atgagtatga gagatgtgtc attcatttgt atcaatgaat gaatgaggac aattagtgta     420
taaatcctta gtacaacaat ctgagggtag gggtggtact attcaatttc tatttataaa     480
gatacttatt tctatttatt tatgcttgtg acaaatgttt tgttcgggac cacaggaatc     540
acaaagatga gtctttgaat ttaagaagtt aatggtccag gaataattac atagcttaca     600
aatgactatg ataccatc aaacaagagg ttccatgaga aaataatctg aaaggtttaa     660
taagttgtca aaggtgagag ggctcttctc tagctagaga ctaatcagaa atacattcag     720
ggataattat ttgaatagac cttaagggtt gggtacattt tgttcaagca ttgatggaga     780
aggagagtga atatttgaaa acattttcaa ctaaccaacc acccaatcca acaaacaaaa     840
aatgaaaaga atctcagaaa cagtgagata agagaaggaa ttttctcaca acccacacgt     900
atagctcaac tgctctgaag aagtatatat ctaatattta acactaacat catgctaata     960
atgataataa ttactgtcat tttttaatgt ctataagtac caggcattta gaagatatta    1020
ttccatttat atatcaaaat aaacttgagg ggatagatca ttttcatgat atatgagaaa    1080
aattaaaaat cagattgaat tatttgcctg tcatacagct aataattgac cataagacaa    1140
ttagatttaa attagttttg aatctttcta ataccaaagt tcagtttact gttccatgtt    1200
```

```
gcttctgagt ggcttcacag acttatgaaa aagtaaacgg aatcagaatt acatcaatgc   1260
aaaagcattg ctgtgaactc tgtacttagg actaaacttt gagcaataac acatatagat   1320
tgaggattgt ttgctgttag tatacaaact ctggttcaaa gctcctcttt attgcttgtc   1380
ttggaaaatt tgctgttctt catggtttct cttttcactg ctatctattt ttctcaacca   1440
ctcacatggc tacaataact gtctgcaagc ttatgattcc caaatatcta tctctagcct   1500
caatcttgtt ccagaagata aaagtagta ttcaaatgca catcaacgtc tccacttgga   1560
gggcttaaag acgtttcaac atacaaaccg gggagttttg cctggaatgt ttcctaaaat   1620
gtgtcctgta gcatataggg tcctcttgtt ccttaaaatc taattacttt tagcccagtg   1680
ctcatcccac ctatggggag atgagagtga aagggagcc tgattaataa ttacactaag   1740
tcaataggca tagagccagg actgtttggg taaactggtc actttatctt aaactaaata   1800
tatccaaaac tgaacatgta cttagttact aagtctttga ctttatctca ttcataccac   1860
tcagctttat ccaggccact tatttgacag tattattgcg aaaacttcct aactggtctc   1920
cttatcatag tcttatcccc ttttgaaaca aagagacag tttcaaaata caaatatgat   1980
ttttattagc tcccttttgt tgtctataat agtcccagaa ggagttataa actccattta   2040
aaaagtcttt gagatgtggc ccttgccaac tttgccagga attcccaata tctagtattt   2100
tctactatta aactttgtgc ctcttcaaaa ctgcattttc tctcattccc taagtgtgca   2160
ttgttttccc ttaccggttg gttttccac cacctttac attttcctgg aacactatac   2220
cctccctctt catttggccc acctctaatt ttctttcaga tctccatgaa gatgttactc   2280
tcgagcattc atcaaatgtt gctgagtcct ggctatgaac cagacactgt gaaagccttt   2340
gggatatttt gccatgctt gggcaagctt atatagtttg cttcataaaa ctctatttca   2400
gttcttcata actaatactt catgactatt gcttttcagg tattccttca taacaaatac   2460
tttggctttc atatatttga gtaaagtccc ccttgaggaa gagtagaaga actgcacttt   2520
gtaaatacta tcctggaatc caaacggata gacaaggatg gtgctacctc tttctggaga   2580
gtacgtgagc aaggcctgtt ttgttaacat gttccttagg agacaaaact taggagagac   2640
acgcatagca gaaaatggac aaaaactaac aaatgaatgg gaattgtact tgattagcat   2700
tgaagacctt gttatacta tgataaatgt ttgtatttgc tggaagtgct actgacggta   2760
aacccttttt gtttaaatgt gtgccctagt agcttgcagt atgatctatt ttttaagtac   2820
tgtacttagc ttatttaaaa attttatgtt taaaattgca tagtgctctt tcattgaaga   2880
agttttgaga gagagataga attaaattca cttatcttac catctagaga aacccaatgt   2940
taaaactttg ttgtccatta tttctgtctt ttattcaaca ttttttttag agggtgggag   3000
gaatacagag gaggtacaat gatacacaaa tgagagcact ctccatgtat tgttttgtcc   3060
tgtttttcag ttaacaatat attatgagca tatttccatt tcattaaata ttcttccaca   3120
aagttatttt gatggctgta tatcacccta ctttatgaat gtaccatatt aatttatttc   3180
ctggtgtggg ttatttgatt ttataatctt acctttagaa taatgaaaca cctgtgaagc   3240
tttagaaaat actggtgcct gggtctcaac tccacagatt ctgatttaac tggtctgggt   3300
tacagactag gcattgggaa ttcaaaaagt tcccccagtg attctaatgt gtagccaaga   3360
tcgggaaccc ttgtagacag ggatgatagg aggtgagcca ctcttagcat ccatcattta   3420
gtattaacat catcatcttg agttgctaag tgaatgatgc acctgaccca ctttataaag   3480
acacatgtgc aaataaaatt attataggac ttggtttatt agggcttgtg ctctaagttt   3540
tctatgttaa gccatacatc gcatactaaa tactttaaaa tgtaccttat tgacatacat   3600
```

-continued

```
attaagtgaa aagtgtttct gagctaaaca atgacagcat aattatcaag caatgataat    3660
ttgaaatgaa tttattattc tgcaacttag ggacaagtca tctctctgaa ttttttgtac    3720
tttgagagta tttgttatat ttgcaagatg aagagtctga attggtcaga caatgtcttg    3780
tgtgcctggc atatgatagg catttaatag ttttaaagaa ttaatgtatt tagatgaatt    3840
gcataccaaa tctgctgtct tttcttatg gcttcattaa cttaatttga gagaaattaa     3900
ttattctgca acttagggac aagtcatgtc tttgaatatt ctgtagtttg aggagaatat    3960
ttgttatatt tgcaaaataa aataagtttg caagttttttt ttttctgccc caaagagctc   4020
tgtgtccttg aacataaaat acaaataacc gctatgctgt taattattgg caaatgtccc    4080
attttcaacc taaggaaata ccataaagta acagatatac caacaaaagg ttactagtta   4140
acaggcattg cctgaaaaga gtataaaaga atttcagcat gattttccat attgtgcttc   4200
caccactgcc aataacaaaa taactagcaa cggtaccct                          4239

<210> SEQ ID NO 2
<211> LENGTH: 29
<212> TYPE: DNA
<213> ORGANISM: Artificial
<220> FEATURE:
<223> OTHER INFORMATION: Foward primer of AFP1.9

<400> SEQUENCE: 2
cctcgagcat tcatcaaatg ttgctgagt                                       29

<210> SEQ ID NO 3
<211> LENGTH: 30
<212> TYPE: DNA
<213> ORGANISM: Artificial
<220> FEATURE:
<223> OTHER INFORMATION: Reward primer of AFP1.9

<400> SEQUENCE: 3
cctcgaggtt gctagttatt ttgttattgg                                      30

<210> SEQ ID NO 4
<211> LENGTH: 30
<212> TYPE: DNA
<213> ORGANISM: Artificial
<220> FEATURE:
<223> OTHER INFORMATION: Foward primer of AFP2.3

<400> SEQUENCE: 4
gtccctgcag cccctatcac tgaattctta                                      30

<210> SEQ ID NO 5
<211> LENGTH: 32
<212> TYPE: DNA
<213> ORGANISM: Artificial
<220> FEATURE:
<223> OTHER INFORMATION: Reward primer of AFP2.3

<400> SEQUENCE: 5
cctctcgaga gtaacatctt catggagatc tg                                   32

<210> SEQ ID NO 6
<211> LENGTH: 33
<212> TYPE: DNA
<213> ORGANISM: Artificial
<220> FEATURE:
<223> OTHER INFORMATION: Foward primer of AFP2.0

<400> SEQUENCE: 6
```

-continued

```
acctcgagct attcagtcat gatgaatttg aga                              33

<210> SEQ ID NO 7
<211> LENGTH: 33
<212> TYPE: DNA
<213> ORGANISM: Artificial
<220> FEATURE:
<223> OTHER INFORMATION: Reward primer of AFP 2.0

<400> SEQUENCE: 7
gcctcgagtg tgccaaaggc gtgtggggtt gac                              33
```